United States Patent [19]

Speranza et al.

[11] Patent Number: 5,414,087
[45] Date of Patent: May 9, 1995

[54] PREPARATION OF N-ALKYLPIPERAZINES

[75] Inventors: George P. Speranza; James H. Templeton, both of Austin, Tex.

[73] Assignee: Huntsman Corporation, Salt Lake City, Utah

[21] Appl. No.: 87,093

[22] Filed: Jul. 7, 1993

[51] Int. Cl.6 .......................................... C07D 295/03
[52] U.S. Cl. ................................. 544/404; 548/300.1
[58] Field of Search ......................................... 544/404

[56] References Cited

U.S. PATENT DOCUMENTS

| | | | |
|---|---|---|---|
| 3,152,998 | 10/1964 | Moss | 544/358 |
| 3,607,874 | 9/1971 | Fuerst | 544/404 |
| 3,654,370 | 4/1972 | Yeakey | 544/162 |
| 3,948,900 | 4/1976 | Moss | 544/404 |
| 4,757,144 | 7/1988 | Okabe et al. | 544/404 |

*Primary Examiner*—Emily Bernhardt
*Attorney, Agent, or Firm*—Russell R. Stolle; Ron D. Brown

[57] ABSTRACT

Disclosed is a one-step method for preparing N-alkylpiperazines which eliminates the initial preparation and isolation of piperazine which comprises reacting a carbonyl compound and an amine in the presence of hydrogen over a metallic hydrogenation-dehydrogenation catalyst from Group VIII of the Periodic Table such as, for example, nickel, copper, cobalt, chromium, palladium, platinum or ruthenium, alone or in combination with other Group VIII metals or transition metals selected from the group consisting of manganese, iron, zinc, copper and chromium.

7 Claims, No Drawings

PREPARATION OF N-ALKYLPIPERAZINES

FIELD OF THE INVENTION

The present invention relates to the preparation of N-alkylpiperazines. More particularly, this invention provides a convenient one-step method for preparing N-alkylpiperazines which eliminates the usual prerequisite of the preparation and isolation of piperazine.

N-Alkylpiperazines are valuable intermediates in the preparation of many drugs.

BACKGROUND OF THE INVENTION

It is known in the art to manufacture N-alkylpiperazines from piperazine and a carbonyl compound, in the presence of hydrogen, over a nickel catalyst.

Usually, the piperazine is prepared from ethylenediamine, aminoethylethylenediamine, monoethanolamine or diethanolamine by reaction with ammonia over a metal-type hydrogenation-dehydrogenation catalyst, such as, for example nickel or another metal.

The choice of the route is influenced to some extent by the other nitrogen derivatives the producer desires to manufacture. See Kirk-Othmer: *Encyclopedia of Chemical Technology*, 3rd ed., Vol. 2, p. 298, John Wiley, N.Y.

The reaction can be generally represented as follows:

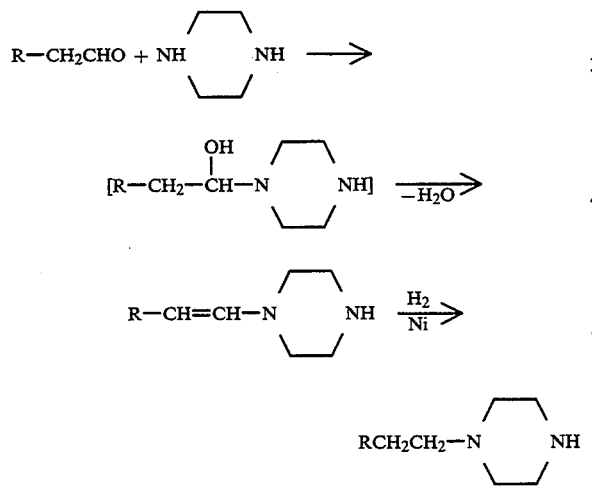

It is also well-known that the reaction of piperazine with carbonyl compounds is not selective and, after hydrogenation of such adducts, the removal of solid piperazine by distillation is tedious.

Piperazine is a solid which melts at 109.6° C. and boils at 148.5° C. Because it is a solid that melts close to its boiling point it is very difficult to isolate it with a high degree of purity by distillation. In the commercial preparation setting, this means that all the lines must be heated so that piperazine does not freeze up in the distillation procedure.

Another problem is that much of the piperazine does not react. For example, in the preparation of isobutylpiperazine from isobutyraldehyde and piperazine, unreacted piperazine will interfere with the isolation and purity of the final product. This is usually addressed by using an excess of isobutyraldehyde, which results in reduced yields of the desired product.

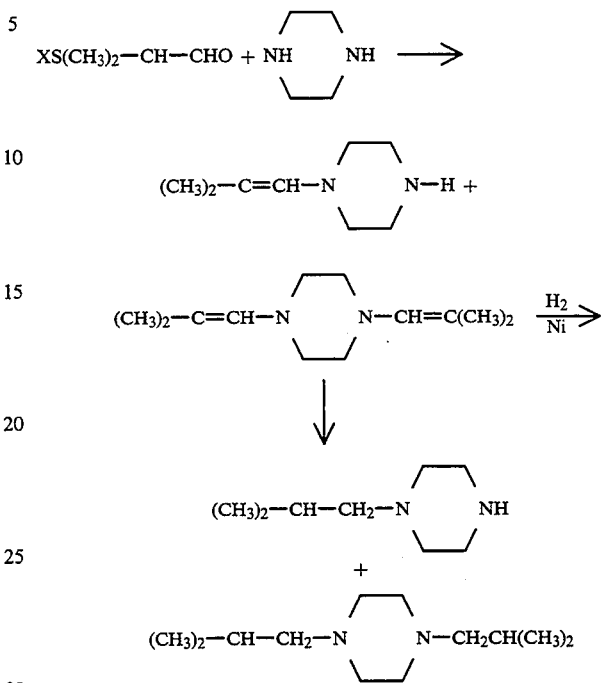

It does not appear that it has been suggested anywhere in the art to manufacture N-alkylpiperazine in a manner which bypasses the production and isolation of piperazine.

Such a method would represent a significant advance in the art because it would reduce costs in a commercial operation due to the fact it would not be necessary to heat distillation lines in conjunction with isolation of the piperazine. Also the use of an excess of isobutyraldehyde would not be necessary.

In the instant invention a carbonyl compound such as isobutyraldehyde is reacted with aminoethylethanolamine over a hydrogenation catalyst to give alkylpiperazine.

SUMMARY OF THE INVENTION

In accordance with the present invention it has been discovered that N-alkylpiperazines can be synthesized directly from carbonyl compounds and amines, thus eliminating the current practice in the art of separately preparing piperazine.

This one-step method of preparation eliminates the necessity of the initial preparation and isolation of piperazine which is somewhat difficult due to its close melting and boiling points.

DETAILED DESCRIPTION OF THE INVENTION

According to the present invention there has been discovered a method for the one-step preparation of N-alkylpiperazines by reacting a carbonyl compound with an amine over a metal hydrogenation-dehydrogenation catalyst, especially of the nickel type.

In particular, this invention comprises a method for reacting carbonyl compounds with amines to produce N-alkylpiperazines in one step. In the preferred embodiment isobutyraldehyde is reacted with aminoethylethanolamine. The reaction can be represented by:

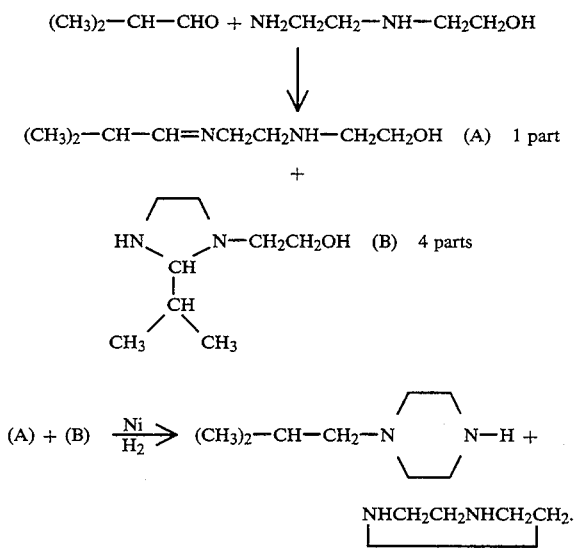

The resulting ratio of the desirable N-alkylpiperazine product to piperazine is much higher than that obtained with the currently available methods.

Amines which are suitable for use as coreactants in the instant invention have the formula:

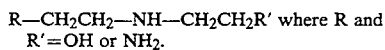

Preferred amines include aminoethylethanolamine, diethylenetriamine and diethanolamine.

The carbonyl compounds suitable as a coreactant in the instant invention have the formula:

where R" or R'=an alkyl group or H. Suitable compounds of this formula include aldehydes and ketones. Preferred aldehydes include formaldehyde, acetaldehyde, propionaldehyde, n-butyaldehyde or isobutyraldehyde. The examples demonstrate good results using isobutyraldehyde.

The ratio of aldehyde or ketone to amine should be in the range of 1.5:1 to 1:10. In the preferred embodiment the ratio was closer to 1:1.

In the product, the ratio of desired N-alkylpiperazine to piperazine is much higher than that usually observed with other available methods. As noted in the examples, the ratio of N-alkylpiperazine to piperazine in the product ranges up to 15:1. This is a very substantial improvement compared with, for example, Comparative Example 1, where the product comprises 21% piperazine and 30% N-isobutylpiperazine by area %.

The reaction takes place in the presence of hydrogen gas. An amount of hydrogen sufficient to hydrogenate the aldehyde coreactant is preferred. In practice, hydrogen gas is preferably passed upflow through the reactor in an amount of 50% excess based on aldehyde feed, in order to obtain complete hydrogenation. Some ammonia may also be added along with the reactants.

The catalyst for use in the process is a metal hydrogenation catalyst. Many metal hydrogenation catalysts are known in the art. The patent literature, for example, shows a number of hydrogenation catalysts which contain metals from Group VIII of the Periodic Table. Such metals may include copper, ruthenium, osmium, cobalt, rhodium, iridium, nickel, palladium and platinum.

Platinum and palladium are often effective at ordinary temperatures. Raney nickel, prepared by dissolving the aluminum from aluminum-nickel alloy with aqueous base effects many hydrogenations at low temperature and pressure.

Another well-known hydrogenation catalyst, copper chromite, contains copper and chromium oxide.

A suitable catalyst may contain a Group VIII metal in combination with one or more transitional metals. Transitional metals which can be employed include manganese, iron, zinc, copper and chromium.

A group VIII metal hydrogenation catalyst which exhibits good results is nickel in combination with one or more transition metals selected from the group consisting of manganese, copper and chromium.

Another Group VIII metal hydrogenation catalyst is cobalt, alone or in combination with one or more transition metals.

The preferred catalyst combination for use in the process is a metal hydrogenation catalyst containing nickel, copper and chromium. Such a catalyst is described, for example, in U.S. Pat. No. 3,152,998, incorporated herein by reference. The catalyst is prepared by the reduction of a mixture of the oxides of nickel, copper and chromium in the presence of hydrogen at a temperature within the range of about 250° C. to 400° C. Calculated on an oxide-free basis, the catalyst contains 60–85 mol% nickel, 14–37 mol % copper and 1–5 mol % chromium. A particularly preferred catalyst composition is one containing 70–80 mol % nickel, 20–25 mol % copper and 1–5 mol % chromium.

The process is conducted at a temperature within the range of from 25° C. to 300° C., with a preferred range being from 70° C. to 250° C. The pressure may vary from 500 to 4500 psi with the preferred range being 1000 to 3000 psi.

The process may be conducted with or without a solvent. Solvents which may be employed include alcohols and water. A preferred solvent is the alcohol corresponding to the carbonyl compound such as isobutanol when isobutyraldehyde is used.

The liquid hourly space velocity should be from about 5 to 0.1 g total liquid feed/hr/ml of catalyst. Preferably the liquid hourly space velocity is about 0.5 g/hr/ml catalyst.

The process may be conducted batchwise, or it may be conducted continuously. Continuous operation is preferred.

Other factors of the invention will become apparent in the course of the following descriptions of exemplary embodiments which are given for illustration of the invention and are not intended to be limiting thereof.

EXAMPLE 1—(N.B. 6777-58)—COMPARATIVE

To a 2-liter 3-necked flask equipped with a stirrer, thermometer and dropping funnel was added 258 g of piperazine and 200 ml of tertiary butanol. Then 216 g of isobutyraldehyde was added allowing the temperature to rise to 60° C. (The mole ratio of reactants is 1:1). 394 grams of this solution was heated with 40 g of a nickel-copper-chromium catalyst (as discussed in U.S. Pat. No.

3,654,370) and hydrogenated at 2500 psig of hydrogen pressure. The product was analyzed by gas phase chromatography and contained 21% piperazine and 30% N-isobutylpiperazine by area percent. Separation of piperazine from the isobutylpiperazine was difficult (even though the isobutylpiperazine boiled at 182° C.) because piperazine deposited throughout the distillation train.

EXAMPLE 2 (6777-60)

To a 1-liter three-necked flask equipped with a stirrer, thermometer and dropping funnel was added 208 g of aminoethylethanolamine. Isobutyraldehyde, 144 g, was added over a 30 minute period, allowing the temperature to rise to 60° C. This material was hydrogenated as in Example 1. Although the main product was the isobutyl derivative of aminoethylethanolamine, the ratio of isobutylpiperazine to piperazine was about 8:1.

EXAMPLE 3 (6777-62)

In this experiment isobutyraldehyde was allowed to react with diethylenetriamine. As in the examples above, the adduct was hydrogenated over a nickel-copper-chromium catalyst in a 1-liter stirred autoclave. The ratio of isobutylpiperazine to piperazine was about 4:1.

EXAMPLE 4 (6777-88)

Isobutyraldehyde was allowed to react with diethanolamine, and the cyclic product formed,

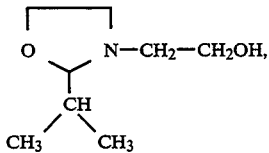

was first hydrogenated at 180° C. and 2000 psig hydrogen. In this run 309 grams of cyclic product and 40 g of nickel catalyst were used. Then 72 g of ammonia was added and the mixture heated at 200° C. along with hydrogen at about 1500 psi pressure. The product contained about 15% N-isobutylpiperazine and piperazine.

EXAMPLE 5 (6777-77)

Aminoethylethanolamine was allowed to react with formaldehyde, and the product was heated with hydrogen over the nickel-copper-chrome catalyst. The ratio of N-methylpiperazine to piperazine was about 11 to 1.

Examples 6 and 7 demonstrate, in addition to utility of the reaction, conditions for conducting the reaction in a continuous reactor. Tables 1 and 2 record results from two series of runs.

EXAMPLE 6

In a typical experiment, isobutyraldehyde and aminoethylethanolamine (AEEA) were pumped separately from weighed feed tanks using adjustable metering pumps. Isobutyraldehyde was pumped at a rate of 0.29 lb/hr and AEEA at a rate of 0.37 lb/hr, giving an isobutyraldehyde/AEEA feed mole ratio of approximately 1.10/1 and a liquid hourly space velocity of 0.5 g total liquid feed/hr/ml catalyst. The two liquid feeds were brought together and allowed to react in a 6-foot coil of ¼-inch tubing before entering the main reactor. Maximum temperature in this coil of tubing was 64° C.

The intermediate formed by the reaction of aldehyde and AEEA was then passed upflow through a Dow-therm-jacketed tubular reactor containing 600 ml of Ni—Cu—Cr catalyst. Hydrogen gas was also passed upflow through the catalyst bed at a rate of 60 liters/hour at STP, giving 50% excess based on aldehyde feed rate. Reactor pressure was maintained at 2000 psig and temperature was increased in 10° increments in the range 160° to 220° C. The intent was to hydrogenate the intermediate product and then close the ring to give the desired N-isobutylpiperazine product.

When operating at each temperature, conditions were held steady for a 2 hour prerun period before collecting products for 2 hours during an on-stream period.

Products were sampled and analyzed by gas chromatography (see Table 1).

EXAMPLE 7

In a second experiment (Runs 8 through 14), isobutyraldehyde and diethylenetriamine (DETA) were reacted in a similar manner to prepare N-isobutylpiperazine product. Isobutyraldehyde and DETA were pumped separately at rates of 0.29 and 0.37 lb/hr, respectively, giving a feed mole ratio of approximately 1.10 aldehyde/DETA and a space velocity of 0.5 g/hr/ml catalyst. Hot spot in the mixing coil was 82° C. before entering the hydrogenation reactor.

The intermediate was then passed up through the same 600 ml of catalyst described in Example 1 and mixed with 50% excess hydrogen gas to obtain complete hydrogenation. Reaction pressure was again held at 2000 psig and reaction temperatures were increased in 10° increments in the range 160° to 220° C.

Two-hour samples were collected at all temperatures after 2-hour prerun periods (Table 2).

Products were sampled and analyzed by gas chromatography. "In Table 1 and Table 2 below, the term 'NEP' is N-ethylpiperazine."

TABLE 1

SUMMARY OF RESULTS
AEEA + ISOBUTYRALDEHYDE → NIBP

| RUN | TEMP. (°C.) | MOLE RATIO ALD./AEEA | YIELD, %, BASIS CONV. DETA | | |
|---|---|---|---|---|---|
| | | | NIBP | PIP | NBP |
| 1 | 160 | 1.19 | 38.2 | 3.5 | 4.4 |
| 2 | 170 | 1.19 | 36.5 | 5.5 | 6.1 |
| 3 | 183 | 0.96 | 28.6 | 4.8 | 13.1 |
| 4 | 190 | 1.32 | 27.7 | 1.8 | 13.6 |
| 5 | 200 | 1.09 | 14.7 | 1.8 | 7.3 |
| 6 | 210 | 1.29 | 10.0 | 3.4 | 8.3 |
| 7 | 220 | 1.14 | 8.2 | 0.5 | 3.6 |

Pressure = 2000 psig
LHSV = 0.50–0.58 g/hr/ml Cat.
AEEA Conversion = 100%

TABLE 2

SUMMARY OF RESULTS
DETA + ISOBUTYRAIMERYDE → NIBP

| RUN | TEMP. (°C.) | MOLE RATIO ALD./ DETA | % DETA CONVERSION | YIELD, %, BASIS CONV. DETA | | |
|---|---|---|---|---|---|---|
| | | | | NIBP | PIP | NEP |
| 8 | 160 | 0.98 | 88.6 | 13.5 | 32.6 | 0.4 |
| 9 | 170 | 1.15 | 91.6 | 19.6 | 43.5 | 2.4 |
| 10 | 180 | 1.11 | 100 | 20.6 | 22.8 | 6.3 |
| 11 | 190 | 1.07 | 100 | 14.7 | 8.7 | 7.4 |
| 12 | 200 | 1.06 | 100 | 15.1 | 6.6 | 10.3 |
| 13 | 210 | 1.21 | 100 | 12.8 | 6.4 | 7.8 |

TABLE 2-continued

SUMMARY OF RESULTS
DETA + ISOBUTYRAIMERYDE → NIBP

| RUN | TEMP. (°C.) | MOLE RATIO ALD./ DETA | % DETA CON- VERSION | YIELD, %, BASIS CONV. DETA | | |
|---|---|---|---|---|---|---|
| | | | | NIBP | PIP | NEP |
| 14 | 221 | 1.11 | 100 | 9.4 | 1.3 | 5.3 |

Pressure = 2000 psig
LHSV = 0.48-0.55 g/hr/ml Cat.

What is claimed is:

1. A one-step method for preparing N-alkylpiperazines, eliminating the need for the initial preparation and isolation of piperazine, comprising reacting a carbonyl compound of the formula:

where R'' and R' = an alkyl group or H; and an amine of the formula:

$NH_2-CH_2CH_2-NH-CH_2CH_2R'''$ where R''' is OH or $NH_2$;

in the presence of hydrogen over a metal hydrogenation catalyst consisting essentially of nickel, copper and chromium.

2. The method of claim 1 wherein the catalyst consists essentially of 60-85 mol % nickel, 14-37 mol % copper and 1-5 mol % chromium.

3. The method of claim 1 wherein the catalyst consists essentially of 70-80 mol % nickel, 20-25 mol % copper and 1-5 mol % chromium.

4. The method of claim 1 wherein the carbonyl compound is selected from the group consisting of isobutyraldehyde, acetone and formaldehyde.

5. The method of claim 4 wherein the carbonyl compound is isobutyraldehyde.

6. The method of claim 1 wherein the amine is selected from the group consisting of aminoethylethanolamine and diethylenetriamine.

7. The method of claim 6 wherein the amine is aminoethylethanolamine.

* * * * *